US012805838B2

(12) United States Patent
Zhu et al.

(10) Patent No.: US 12,805,838 B2
(45) Date of Patent: Nov. 24, 2026

(54) ULTRASONIC PROBE AND ULTRASONIC DIAGNOSTIC DEVICE

(71) Applicant: WUHAN UNITED IMAGING HEALTHCARE CO., LTD., Wuhan (CN)

(72) Inventors: Zhihao Zhu, Wuhan (CN); Changxing Ke, Wuhan (CN); Kang Si, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 62 days.

(21) Appl. No.: 18/733,954

(22) Filed: Jun. 5, 2024

(65) Prior Publication Data

US 2024/0398378 A1 Dec. 5, 2024

(30) Foreign Application Priority Data

Jun. 5, 2023 (CN) ......................... 202310660064.3

(51) Int. Cl.
*A61B 8/00* (2006.01)
*A61B 8/12* (2006.01)

(52) U.S. Cl.
CPC .......... *A61B 8/4444* (2013.01); *A61B 8/4272* (2013.01); *A61B 8/12* (2013.01); *A61B 8/4281* (2013.01)

(58) Field of Classification Search
CPC ........................................................ A61B 8/12
See application file for complete search history.

(56) References Cited

U.S. PATENT DOCUMENTS

| | | | | |
|---|---|---|---|---|
| 5,176,140 | A | 1/1993 | Kami et al. | |
| 5,792,058 | A | 8/1998 | Lee et al. | |
| 8,188,607 | B2 | 5/2012 | Lin et al. | |
| 11,076,838 | B2 | 8/2021 | Morimoto et al. | |
| 2003/0028105 | A1* | 2/2003 | Miller ...................... | A61B 8/12 600/437 |
| 2005/0203399 | A1 | 9/2005 | Vaezy et al. | |
| 2006/0058676 | A1* | 3/2006 | Yagi ..................... | G01N 29/225 600/459 |
| 2006/0184035 | A1 | 8/2006 | Kimura et al. | |
| 2007/0016064 | A1 | 1/2007 | Yamashita et al. | |

(Continued)

FOREIGN PATENT DOCUMENTS

| | | |
|---|---|---|
| CN | 202256939 U | 5/2012 |
| CN | 112654293 A | 4/2021 |

(Continued)

OTHER PUBLICATIONS

First Office Action of counterpart Chinese Patent Application No. 202310660064.3 issued on Dec. 23, 2025.

(Continued)

*Primary Examiner* — Colin T. Sakamoto

(57) ABSTRACT

The present disclosure relates to an ultrasonic probe and an ultrasonic diagnostic device. The ultrasonic probe includes a transducer configured to transmit and receive ultrasonic signals, a housing, and a support member. The support member includes one end connected to the housing and another end connected to the transducer. By arranging the support member, the transducer is connected to the housing through the support member.

17 Claims, 5 Drawing Sheets

(56) References Cited

U.S. PATENT DOCUMENTS

| | | | | |
|---|---|---|---|---|
| 2007/0266792 | A1* | 11/2007 | Oosawa | A61B 8/4488 73/661 |
| 2009/0030325 | A1* | 1/2009 | Hyuga | A61B 8/4488 600/459 |
| 2015/0065883 | A1 | 3/2015 | Lee et al. | |
| 2019/0133559 | A1 | 5/2019 | Okada et al. | |
| 2020/0337675 | A1 | 10/2020 | Sato | |
| 2020/0352545 | A1* | 11/2020 | Yoshida | A61B 8/12 |
| 2021/0219957 | A1* | 7/2021 | Yoshida | B06B 1/064 |

FOREIGN PATENT DOCUMENTS

| | | | |
|---|---|---|---|
| CN | 215914910 | U | 3/2022 |
| CN | 220045929 | U | 11/2023 |
| WO | 2009050881 | A1 | 4/2009 |
| WO | 2013077101 | A1 | 5/2013 |

OTHER PUBLICATIONS

Xiaoxiao Li et al., Design of New Type of Three-row Multi-functional Medical Ultrasound Probe, Journal of Chengdu University (Natural Science Edition), Mar. 30, 2015, pp. 80-83, vol. 34, No. 1.

* cited by examiner

ULTRASONIC PROBE AND ULTRASONIC DIAGNOSTIC DEVICE

CROSS-REFERENCE TO RELATED APPLICATIONS

The present application claims the priority to Chinese Patent Application No. 202310660064.3, filed on Jun. 5, 2023, which is incorporated by reference herein in its entirety.

TECHNICAL FIELD

The present disclosure relates to the field of medical device technology, particularly to an ultrasonic probe and ultrasonic diagnostic device.

BACKGROUND

Ultrasonic diagnostic devices are used to transmit ultrasonic signals to specific parts of an object, receive ultrasonic signals (ultrasonic echo signals) reflected from the object, and thereby acquire organ images of the object in a non-invasive way based on the received ultrasonic signals. The ultrasonic diagnostic device includes an ultrasonic probe, which transmits ultrasonic signals to the object and receives ultrasonic signals reflected from the object.

SUMMARY

The first aspect of the present disclosure provides an ultrasonic probe. The ultrasonic probe includes a transducer configured to transmit and receive ultrasonic signals, a housing, and a support member. The support member includes one end connected to the housing and another end connected to the transducer.

In some embodiments, one of the transducer and the support member has a protrusion, and the other has a groove. The protrusion engages with the groove.

In some embodiments, the support member has a first surface and the transducer has a second surface, one of the first surface or the second surface is provided with the protrusion and the other is provided with the groove, and the first surface is inclined relative to a first direction to define an installation angle of the transducer, where the first direction is a length direction of the housing.

In some embodiments, the support member has a first surface and the transducer has a second surface, one of the first surface or the second surface is provided with the protrusion and the other is provided with the groove, the first surface of the support member includes two first surface parts, the protrusion or the groove is arranged between the two first surface parts, and an angle formed by the two first surface parts is greater than or equal to a field of view angle of the ultrasonic probe.

In some embodiments, the protrusion has a curved surface protruding outwardly, and the groove has a curved surface recessed inwardly.

In some embodiments, the support member is made of a thermally conductive material.

In some embodiments, the ultrasonic probe further includes a heat dissipation device arranged inside the housing. The support member is made of a thermally conductive material and connected to the heat dissipation device.

In some embodiments, the support member is arranged within a receiving cavity formed by at least one of the transducer or the housing and connected to a cavity wall of the receiving cavity.

In some embodiments, the cavity wall of the receiving cavity is provided with an adhesive sump extending along a second direction, the support member is located within the adhesive sump, and the adhesive sump is configured to receive adhesive connecting the support member and the housing, where the second direction is perpendicular to a first direction and the first direction is a length direction of the housing.

In some embodiments, the transducer includes a curved backing layer connected to the support member, with an axial direction of the backing layer being perpendicular to the second direction and the first direction.

In some embodiments, the ultrasonic probe further includes a positioning arrangement. The positioning arrangement includes a positioning groove and a positioning protrusion, one of which is provided on a sump wall of the adhesive sump and the other of which is provided on the support member, and the positioning protrusion engages with the positioning groove.

In some embodiments, the transducer includes a backing layer, an electrical connection layer, a piezoelectric layer, a matching layer, and an acoustic lens layer sequentially arranged and connected. The backing layer is connected to the support member, and at least one end of the acoustic lens layer extends into and engages with the housing.

In some embodiments, the ultrasonic probe further includes cables extending through the housing. The electrical connection layer is connected with electrical connection leads, and the electrical connection leads are connected with the cables. The electrical connection leads are provided in multiple, the cables are provided in multiple, the multiple electrical connection leads and the multiple cables are arranged at intervals along a fourth direction, and the multiple electrical connection leads and the multiple cables are soldered to form solder joints in one-to-one correspondence, where the fourth direction forms an angle with respect to the first direction and the first direction is a length direction of the housing. Adjacent two of the solder joints are staggered in the fourth direction.

In some embodiments, the ultrasonic probe further includes cables extending through the housing. The electrical connection layer is connected with electrical connection leads, and the electrical connection leads are connected with the cables through a connector.

The second aspect of the present disclosure provides an ultrasonic diagnostic device including an ultrasonic probe according to any one embodiments as described above.

The third aspect of the present disclosure provides an ultrasonic probe, which includes a transducer configured to transmit and receive ultrasonic signals, a housing, and a support member arranged within the housing and supporting the transducer. One of the transducer and the support member has a protrusion, and the other has a groove. The protrusion engages with the groove.

Details of one or more embodiments of the present disclosure are set forth in the accompanying drawings and description below. Other features, objects, and advantages of the disclosure will become apparent from the description, the drawings, and the claims.

DETAILED DESCRIPTION

Figure 1:
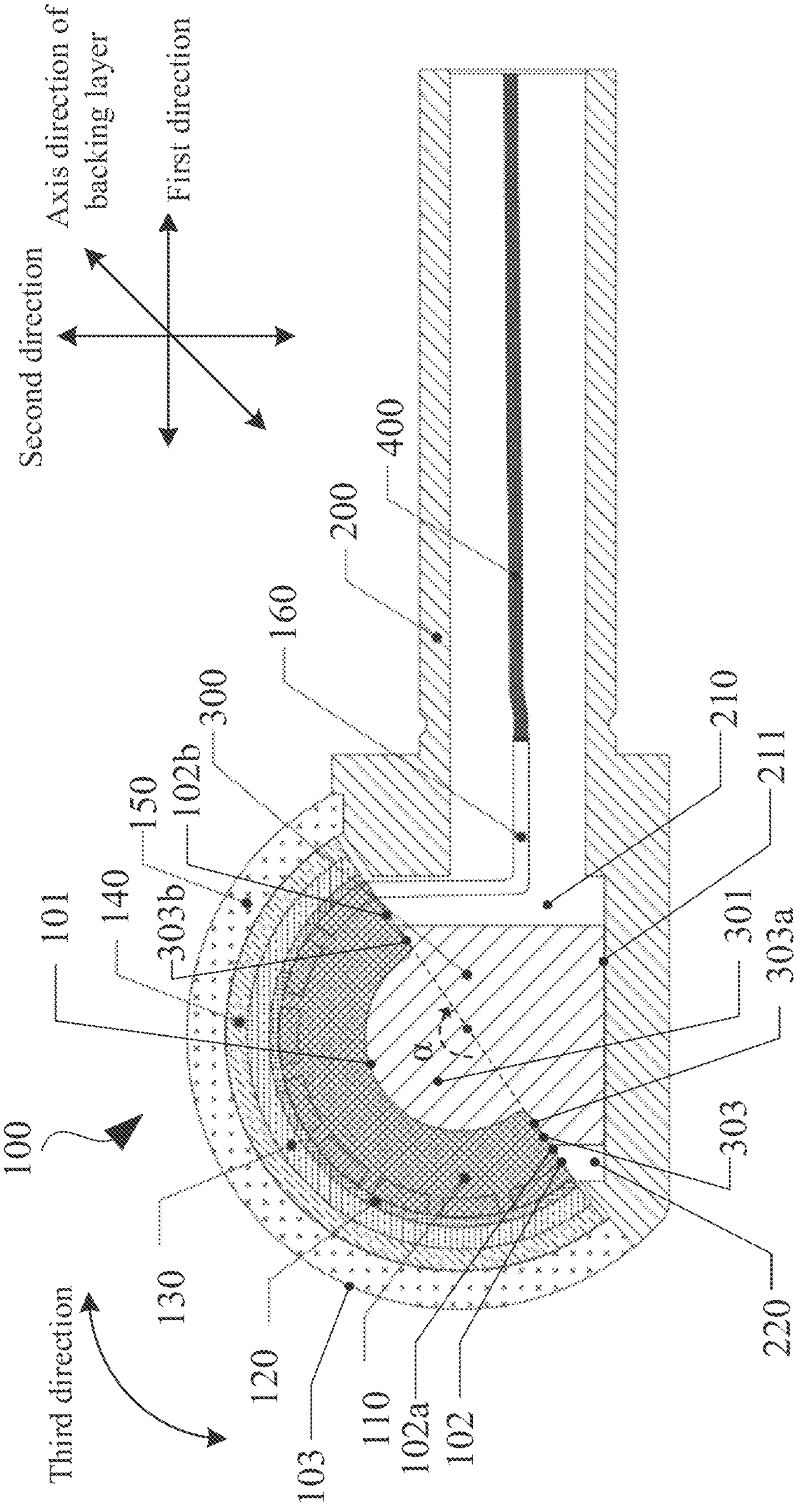
FIG. 1 is a schematic diagram of a structure of an ultrasound probe according to embodiments of the present disclosure.

To make the purposes, features, and advantages of the present disclosure more clearly understood, detailed explanations of specific embodiments of the present disclosure are provided below in conjunction with the accompanying drawings. Many specific details are described below to facilitate a full understanding of the present disclosure. However, the present disclosure can be implemented in many other ways different from those described here. Those skilled in the art can make similar improvements without departing from the essence of the present disclosure. Therefore, the present disclosure is not limited to the specific exemplary embodiments disclosed below.

In the description of the present disclosure, it should be understood that if terms such as “center”, “longitudinal”, “lateral”, “length”, “width”, “thickness”, “top”, “bottom”, “front”, “back”, “left”, “right”, “vertical”, “horizontal”, “top”, “bottom”, “inner”, “outer”, “clockwise”, “counter-clockwise”, “axial”, “radial”, “circumferential”, etc., are used, these terms indicate orientations or positional relationships as shown in the drawings, and are used to describe the present disclosure and simplify the description, not indicating or implying that the described devices or components must have specific orientations, be constructed and operated in specific orientations. Therefore, these terms should not be interpreted as limitations on the present disclosure.

In addition, if terms such as “first”, “second”, etc., are used, these terms are only used to describe the sequence, not indicating or implying relative importance and specific quantities of the described technical features. Therefore, features described with “first”, “second”, etc., may include at least one of those features, whether explicitly stated or implied. In the description of the present disclosure, if the term “multiple” is used, it means at least two, such as two, three, etc., unless otherwise explicitly specified.

In the present disclosure, unless otherwise explicitly specified and limited, terms such as “installation”, “connection”, “coupling”, “fixation”, etc., should be interpreted in a broad sense. For example, it may refer to fixed connections, detachable connections, or integration. It could be mechanical connections or electrical connections. It could be direct connections or indirect connections through an intermedium. It could be internal communication between two components or the interaction relationship between two components, unless otherwise explicitly specified. Ordinary skilled persons in the art can understand the specific meanings of the above terms in the present disclosure based on specific circumstances.

In the present disclosure, unless otherwise explicitly specified and limited, if there is a description such as the first feature being “on” or “under” the second feature, it may mean that the first and second features are in direct contact, or the first and second features are in contact indirectly through an intermedium. Additionally, the first feature being “above”, “on top of”, or “on” the second feature may mean that the first feature is directly above or diagonally above the second feature, or it may simply indicate that the horizontal height of the first feature is higher than that of the second feature. The first feature being “below”, “underneath”, or “beneath” the second feature may mean that the first feature is directly below or diagonally below the second feature, or it may simply indicate that the horizontal height of the first feature is lower than that of the second feature.

It should be noted that if a component is described to be “fixed to” or “set on” another component, it may be directly on the other component or there may also be an intermedium component. If a component is considered to be “connected to” another component, it can be directly connected to the other component or there may also be an intermedium component. If present, the terms “vertical”, “horizontal”, “above”, “below”, “left”, “right”, and similar expressions used in the present disclosure are for illustrative purposes and do not imply that they are the only embodiments.

Ultrasonic diagnostic devices are used to transmit ultrasonic signals to specific parts of an object, receive ultrasonic signals (ultrasonic echo signals) reflected from the object, and thereby acquire images of organs in the object in a non-invasive way based on the received reflected ultrasonic signals. The ultrasonic diagnostic device includes an ultrasonic probe, which transmits ultrasonic signals to the object and receives ultrasonic signals reflected from the object.

In the related technology, the ultrasonic probe includes a transducer and a housing that are connected to each other. There are two connection methods for the transducer and the housing. The first method involves filling adhesive between the transducer and the housing to support and fix the transducer. However, with the first method, the positional relationship between the transducer and the housing is controlled only by the shape of the cured adhesive, leading to inaccuracies in the installation position of the transducer. In addition, bubbles may be introduced during the assembly of the ultrasonic probe, resulting in significant errors in the shape of the cured adhesive. Additionally, in the first connection method, due to the adhesive filled between the transducer and the housing, it is difficult to provide heat dissipation for the transducer or transfer heat to the housing, resulting in a heat dissipation issue for the transducer.

The second method involves processing a backing layer of the transducer into a structural component, connecting the backing layer to the housing, and using the backing layer to support the remaining components of the transducer. However, with the second method, there are requirements for the material of the backing layer, the shape of the backing layer, and the machining accuracy of the housing, which leads to greater difficulties in the manufacturing process of the transducer. Additionally, with the second connection method, it is required to improve the structure of the transducer to provide space for setting up the heat dissipation structure, while ensuring accurate positioning and connection between the backing layer and the housing, which further increases the manufacturing difficulty of the transducer.

The present disclosure provides an ultrasound probe, as shown in FIG. 1, which includes a transducer 100, a housing 200, and a support member 300. The transducer 100 is configured to transmit and receive ultrasonic signals. The support member 300 includes one end connected to the housing 200 and another end connected to the transducer 100. Through the support member 300, the transducer 100 is connected to the housing 200.

In some embodiments, the support member 300 is arranged within a receiving cavity formed by at least one of the transducer 100 or the housing 200. Exemplarily, as shown in FIG. 1, the housing 200 has a receiving cavity 210, and the support member 300 is arranged within the receiving cavity 210. One end of the support member 300 is connected to a cavity wall 211 of the receiving cavity 210 and another end of the support member 300 is connected to the transducer 100. The cavity wall 211 may include, for example, at least one of a bottom wall or a lateral sidewall of the receiving cavity 210. The receiving cavity 210 is covered by at least one component of the transducer 100. In alternative embodiments, the receiving cavity can be formed by the transducer 100, or collectively by the transducer 100 and the housing 200.

According to the embodiment as shown in FIG. 1, in the ultrasound probe, the support member 300 is arranged within the receiving cavity 210 of the housing 200, with one end of the support member 300 connected to the cavity wall of the receiving cavity 210 and another end connected to the transducer 100, thereby achieving the connection between the transducer 100 and the housing 200. Compared with the existing first connection method as mentioned above, the ultrasound probe provided in the present disclosure does not require a large amount of adhesive to be filled in the receiving cavity 210 for directly bonding the transducer 100. Rather, only a small amount of adhesive is needed to bond the support member 300 to achieve the connection between the transducer 100 and the housing 200. By arranging the support member 300 between the transducer 100 and the housing 200, the connection between the transducer 100 and the housing 200 is realized, and the positional relationship between the transducer 100 and the housing 200 is fixed after the connection. Compared with the existing second connection method as mentioned above, it only needs to provide the support member 300 to connect the transducer 100 and the housing 200 according to the ultrasound probe of the present disclosure, and the support member 300 also supports the transducer 100 without changing the structure of the transducer 100, thereby reducing the manufacturing difficulty of the transducer 100. In contrast, in an ultrasound probe without the support member 300, space needs to be reserved on the transducer 100 and the housing 200 for the assembly and connection of the two, and there is a limit to the minimum sizes of mounting portions for the connection between the transducer 100 and the housing 200. In the present disclosure, the support member 300 are arranged within the receiving cavity 210, allowing the transducer 100 to be connected to the housing 200 through the support member 300, eliminating the space requirements for the direct assembly of the transducer 100 and the housing 200 and making the finished ultrasound probe more compact and smaller in size.

In some embodiments, a side wall of the housing 200 close to the transducer 100 is recessed inwardly to form the receiving cavity 210. The support member 300 is arranged within the receiving cavity 210 and is connected to an inner wall of the housing 200, thereby arranging the support member 300 on one side of the housing 200.

Specifically, as shown in FIG. 1, one of the transducer 100 and the support member 300 has a protrusion 301 while the other has a groove 101, and the protrusion 301 engages with the groove 101 to limit the relative positions of the transducer 100 and the support member 300. By providing an engagement structure between the transducer 100 and the support member 300, with one of the protrusion 301 and the groove 101 of the engagement structure being provided on the transducer 100 and the other on the support member 300, the engagement of the transducer 100 and the support member 300 can be achieved through the engagement structure, thereby limiting the relative positions of the transducer 100 and the support member 300.

In some embodiments, the support member 300 has a first surface 303, and the transducer 100 has a second surface 102. One of the first surface 303 and the second surface 102 includes the protrusion 301, while the other has the groove 101. When the protrusion 301 engages with the groove 101, the first surface 303 and the second surface 102 make face-to-face contact. The first surface 303 is inclined relative to a first direction to define the installation angle of the transducer 100. The first direction is the length direction of the housing 200. When the protrusion 301 engages with the groove 101, the first surface 303 of the support member 300 and the second surface 102 of the transducer 100 make face-to-face contact, thereby limiting the installation angle of the transducer 100 on the support member 300. In addition, the support member 300 is arranged within the receiving cavity 210 of the housing 200, which limits the installation angle of the transducer 100 on the housing 200.

In some embodiments, as shown in FIG. 1, the support member 300 has the first surface 303 with the protrusion 301 protruding outwardly from the first surface 303. The transducer 100 has the second surface 102 with the groove 101 recessed inwardly from the second surface 102. When the protrusion 301 engages with the groove 101, the first surface 303 and the second surface 102 make face-to-face contact to limit the relative positions of the transducer 100 and the support member 300.

In various embodiments, the protrusion 301 can be provided at different positions on the first surface 303, including but not limited to, an edge position, a center portion, or any off-center position on the first surface 303. Similarly, the groove 101 can be provided at different positions on the second surface 102, while corresponding to the position of the protrusion 301 to ensure the engagement therebetween.

In alternative embodiments, the support member 300 has the first surface 303 with a groove recessed inwardly from the first surface 303. The transducer 100 has the second surface 102 with a protrusion protruding outwardly from the second surface 102. When the protrusion engages with the groove, the first surface 303 and the second surface 102 make face-to-face contact to limit the relative positions of the transducer 100 and the support member 300.

In some embodiments, as shown in FIG. 1, a side wall of the support member 300 close to the transducer 100 forms the first surface, and the first surface includes two first surface parts 303*a*, 303*b*. The protrusion 301 or groove 101 is provided between the two first surface parts 303*a*, 303*b*. In some embodiments, the angle α formed by the two first surface parts 303*a*, 303*b* is greater than or equal to the field of view angle of the ultrasonic probe. According to the actual operational requirements of the transducer 100, the angle α formed by the two first surface parts 303*a*, 303*b* is set to be greater than or equal to the field of view angle of the ultrasonic probe, which limits the installation angle of the transducer 100 on the housing 200. In some embodiments, one or both of the two first surface parts 303*a*, 303*b* is inclined relative to the first direction.

It should be noted that the field of view (FOV) angle of the ultrasonic probe is the angle formed between a central plane of the first element of the transducer and a central plane of the last element of the transducer.

Specifically, the transducer 100 includes an acoustic lens layer 150, a matching layer 140, a piezoelectric layer 130, an electrical connection layer 120, and a backing layer 110 stacked in sequence. By cutting the stacked layers, individual elements of transducer 100 are formed, each being able to independently transmit and receive signals. The first element and the last element that are located at outermost positions determine the field of view of the transducer. The transducer 100 has a curved shape (i.e., the ultrasonic probe is a convex array probe), with the angle α formed by the two first surface parts 303*a*, 303*b* being greater than or equal to the field of view angle of the ultrasonic probe.

In some embodiments, as shown in FIG. 1, the protrusion 301 is provided between the two first surface parts 303*a*, 303*b*. The side wall of the transducer 100 close to the support member 300 forms the second surface 102, and the second surface 102 includes two second surface parts 102*a*, 102*b*. The groove 101 is provided between the two second surface parts 102*a*, 102*b*. When the protrusion 301 engages with the groove 101, the two first surface parts 303*a*, 303*b* and the two second surface parts 102*a*, 102*b* make face-to-face contact in one-to-one correspondence. In some embodiments, similar to the first surface parts 303*a*, 303*b*, one or both of the two second surface parts 102*a*, 102*b* is inclined relative to the first direction, correspondingly.

It should be understood that the two first surface parts 303*a*, 303*b* can be either continuous or discontinuous. In the case where the two first surface parts 303*a*, 303*b* are continuous, they are connected to each other and collectively surround the protrusion 301. In the case where the two first surface parts 303*a*, 303*b* are discontinuous, they may be separated by the protrusion 301 as two discrete parts. Similarly, the two second surface parts 102*a*, 102*b* may be either continuous or discontinuous. In the case where the two second surface parts 102*a*, 102*b* are continuous, they are connected to each other and collectively surround the groove 101. In the case where the two second surface parts 102*a*, 102*b* are discontinuous, they may be separated by the groove 101 as two discrete parts. In the case where the two second surface parts 102*a*, 102*b* are continuous, the transducer 100 may have, for example, a hollow hemisphere or domed shape.

In alternative embodiments, the groove is provided between the two first surface parts 303*a*, 303*b*. The side wall of the transducer 100 close to the support member 300 forms the second surface, and the second surface includes two second surface parts 102*a*, 102*b*, and the protrusion is provided between the two second surface parts 102*a*, 102*b*. When the protrusion engages with the groove, the two first surface parts 303*a*, 303*b* and the two second surface parts 102*a*, 102*b* make face-to-face contact in one-to-one correspondence.

In some embodiments, the cross-section of transducer 100 is curved. In this case, the two second surface parts 102*a*, 102*b* of transducer 100 are set at an angle to each other, and the angle between the two second surface parts 102*a*, 102*b* may be acute, right or obtuse. When the protrusion 301 engages with the groove 101, the second surface 102 and the first surface 303 make face-to-face contact. The two second surface parts 102*a*, 102*b* are set at an angle to each other, the two first surface parts 303*a*, 303*b* are also set at an angle to each other, and the angle between the two second surface parts 102*a*, 102*b* is the same as the angle α between the two first surface parts 303*a*, 303*b*.

In some embodiments, as shown in FIG. 1, the cross-section of transducer 100 is semi-circular. The two second surface parts 102*a*, 102*b* of transducer 100 are coplanar with each other, resulting in a 180° angle between the two second surface parts 102*a*, 102*b*. When the protrusion 301 engages with the groove 101, the second surface 102 and the first surface 303 make face-to-face contact. The two second surface parts 102*a*, 102*b* are coplanar with each other, so the two first surface parts 303*a*, 303*b* are also coplanar with each other, i.e., the angle α between the two first surface parts 303*a*, 303*b* is also 180°.

In some embodiments, the two second surface parts of the transducer 100 are provided in parallel. Correspondingly, the two first surface parts of the support member 300 are also provided in parallel, and the corresponding first and second surface parts make face-to-face contact.

In some embodiments, the protrusion 301 and the groove 101 can be of any shape as long as they can achieve engagement. For example, the protrusion 301 and the groove 101 can be cuboid-shaped, cylindrical, or wedge-shaped.

In some embodiments, as shown in FIG. 1, the protrusion 301 has a curved surface protruding outwardly, while the groove 101 has a curved surface recessed inwardly. By configuring both the protrusion and groove with curved structures, the surfaces of the protrusion 301 and groove 101 used for engagement are both curved, which prevents damage to the support member 300 or transducer 100 due to collisions during the engagement of the protrusion 301 and the groove 101. In some embodiments, the curved surface of the protrusion 301 and/or the curved surface of the groove 101 are concentric with an outer surface 103 of the transducer 100.

In some embodiments, the positions of support member 300 and transducer 100 are determined through the engagement of the engagement structure, and adhesive is provided on at least one of the protrusion 301 and the groove 101, which further enhances the connection between transducer 100 and the support member 300.

In some embodiments, the support member 300 is made of a thermally conductive material, enabling it to transfer heat from the transducer 100 to the housing 200. By using thermally conductive material for the support member 300, the support member 300 is thus able to conduct heat, and the heat generated during the operation of the transducer 100 can be transferred to the support member 300, which in turn transfers the heat to the housing 200, thereby reducing the heat on support member 300.

Figure 2:
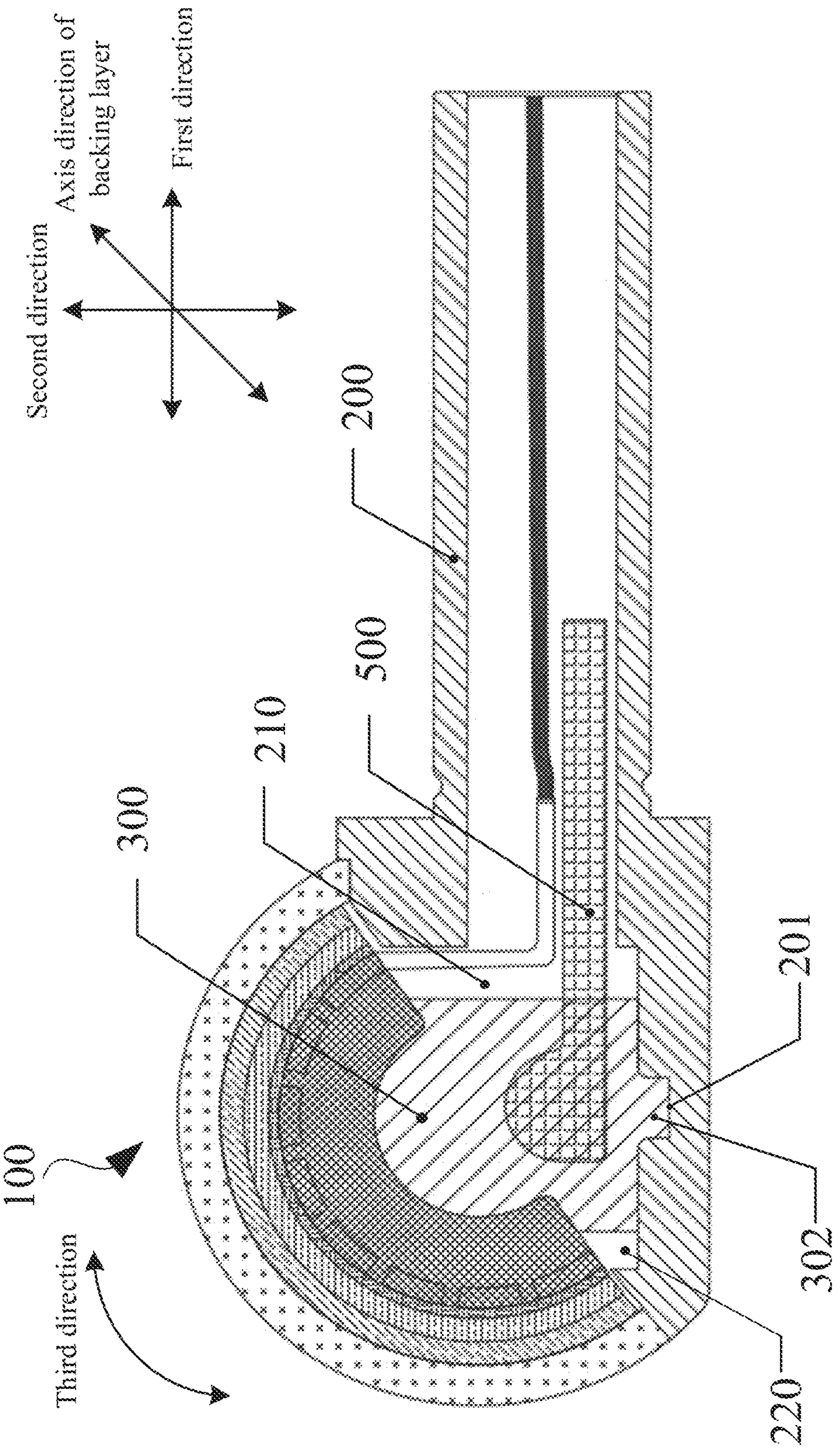
FIG. 2 is a schematic diagram of a structure of an ultrasound probe according to some other embodiments of the present disclosure.

In some embodiments, as shown in FIG. 2, the ultrasonic probe also includes a heat dissipation device 500. The support member 300 is made of a thermally conductive material. The support member 300 is connected to the heat dissipation device 500, and the heat dissipation device 500 extends into the support member 300. The support member 300 transfers the heat from the transducer 100 to the heat dissipation device 500. By using thermally conductive material for the support member 300 and connecting the support member 300 to the heat dissipation device 500, the support member 300 is thus able to conduct heat, and the heat from the transducer 100 is transferred to the heat dissipation device 500 through the support member 300. In alternative embodiments, the support member 300 is connected to the heat dissipation device, and the heat dissipation device abuts at least one side of the support member 300. The heat dissipation device 500 can be made of various thermal conductive materials, such as copper, aluminum, etc.

In some embodiments, as shown in FIGS. 1-2, a cavity wall of the receiving cavity 210 is provided with an adhesive sump 220 having a thickness extending along a second direction, and the support member 300 is located within the adhesive sump 220. The adhesive sump 220 is configured to receive the adhesive connecting the support member 300 and the housing 200. The second direction is perpendicular to the first direction, and the first direction is the length direction of the housing 200. The adhesive sump 220 provided on the cavity wall of receiving cavity 210 facilitates installation of the support member 300, and also receives the adhesive connecting the support member 300 and the housing 200. In other embodiments, the support member 300 can be arranged within the receiving cavity 210 through various mechanical means.

In some embodiments, the transducer 100 includes a curved backing layer 110 that is connected to the support member 300. The axis direction of the backing layer (i.e., an axis of a virtual tube to which the curved backing layer belongs) is perpendicular to the second direction and the first direction. A cavity wall of the receiving cavity 210 on the side away from the transducer 100 is provided with the adhesive sump 220 extending along the second direction. The axis direction of the backing layer 110, the second direction, and the first direction are perpendicular to one another, thereby defining the specific position of the adhesive sump 220.

It should be noted that the backing layer 110 of the transducer 100 is arc-shaped, i.e., the cross-section of the backing layer 110 is fan-shaped, which inherently has an axis. More specifically, as shown in FIG. 1, the backing layer 110 is semi-annular, with a cross-section thereof being a semi-circular structure, and thus the axis direction of the backing layer 110 is perpendicular to the paper.

In some embodiments where the ultrasound probe is a convex array probe, the convex array probe includes an arc-shaped transducer 100, a housing 200, and a support member 300. The transducer 100 is configured to transmit and receive ultrasound signals. The housing 200 has a receiving cavity 210. The support member 300 is arranged within the receiving cavity 210, with one end of the support member 300 connected to a cavity wall of the receiving cavity 210 and another end connected to the transducer 100.

Specifically, the transducer 100 includes an acoustic lens layer 150, a matching layer 140, a piezoelectric layer 130, an electrical connection layer 120, and a backing layer 110 stacked in sequence. By cutting the stacked layers, individual elements of transducer 100 are formed, each being able to independently transmit and receive signals.

In some embodiments, as shown in FIG. 2, the ultrasound probe also includes a positioning arrangement, which includes a positioning groove 201 and a positioning protrusion 302. One of the positioning groove 201 and the positioning protrusion 302 is provided on a sump wall of the adhesive sump 220 extending along the first direction (i.e., the bottom wall of the adhesive sump 220), while the other is provided on the support member 300. The positioning protrusion 302 engages with the positioning groove 201, thereby determining the position of the support member 300 within the adhesive sump 220. Exemplarily, as shown in FIG. 2, the positioning groove 201 is provided on the sump wall of the adhesive sump 220 extending along the first direction, while the positioning protrusion 302 is provided on the support member 300.

In some embodiments, the support member 300 and the sump wall of the adhesive sump 220 extending along the first direction are fixed with adhesive. In some embodiments, the support member 300 and the sump wall of the adhesive sump 220 extending along the first direction are connected by fasteners.

Specifically, as shown in FIG. 1, the transducer 100 includes a backing layer 110, an electrical connection layer 120, a piezoelectric layer 130, a matching layer 140, and an acoustic lens layer 150 sequentially arranged and connected. The backing layer 110 is connected to the support member 300, and at least one end of the acoustic lens layer 150 in a third direction extends into and engages with the housing 200. By increasing the length of the acoustic lens layer 150 in the third direction, it ensures that the ultrasound signals are maintained within a designed range. Moreover, at least one end of the acoustic lens layer 150 in the third direction extends into and engages with the housing 200, which further limits the movement of the acoustic lens layer 150 in the third direction. The third direction is the extension direction of the acoustic lens layer 150.

Specifically, after at least one end of the acoustic lens layer 150 in the third direction extends into and engages with the housing 200, the acoustic lens layer 150 is fixed to the housing 200 with adhesive. In some embodiments, the acoustic lens layer 150 can be formed directly by filling adhesive and then curing the same.

That is, the transducer 100 is engaged with the support member 300 through the groove 101 and protrusion 301, and the ends of the transducer 100 in the third direction are connected to the housing 200 with adhesive.

Figure 3:
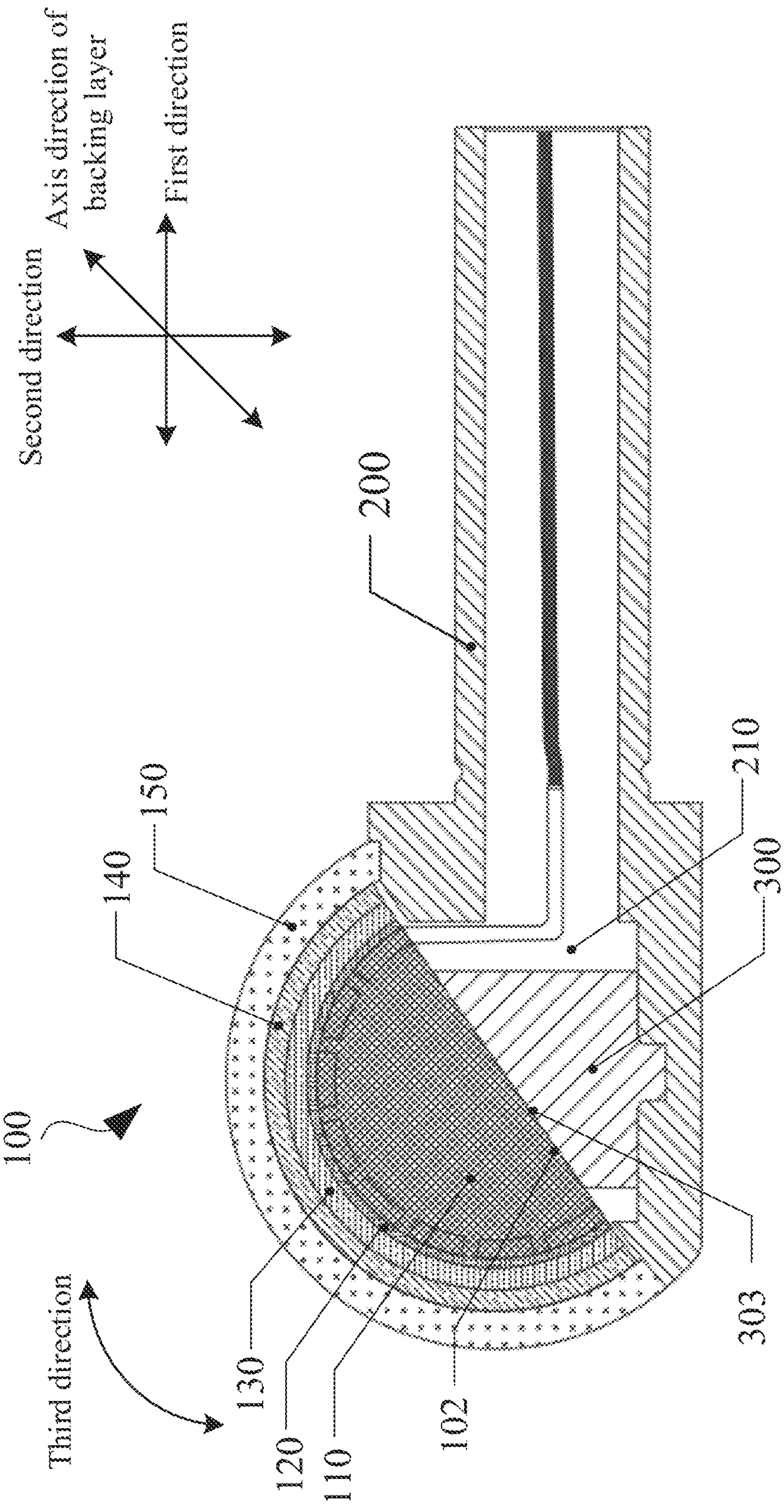
FIG. 3 is a schematic diagram of a structure of an ultrasound probe according to some other embodiments of the present disclosure.
Figure 4:
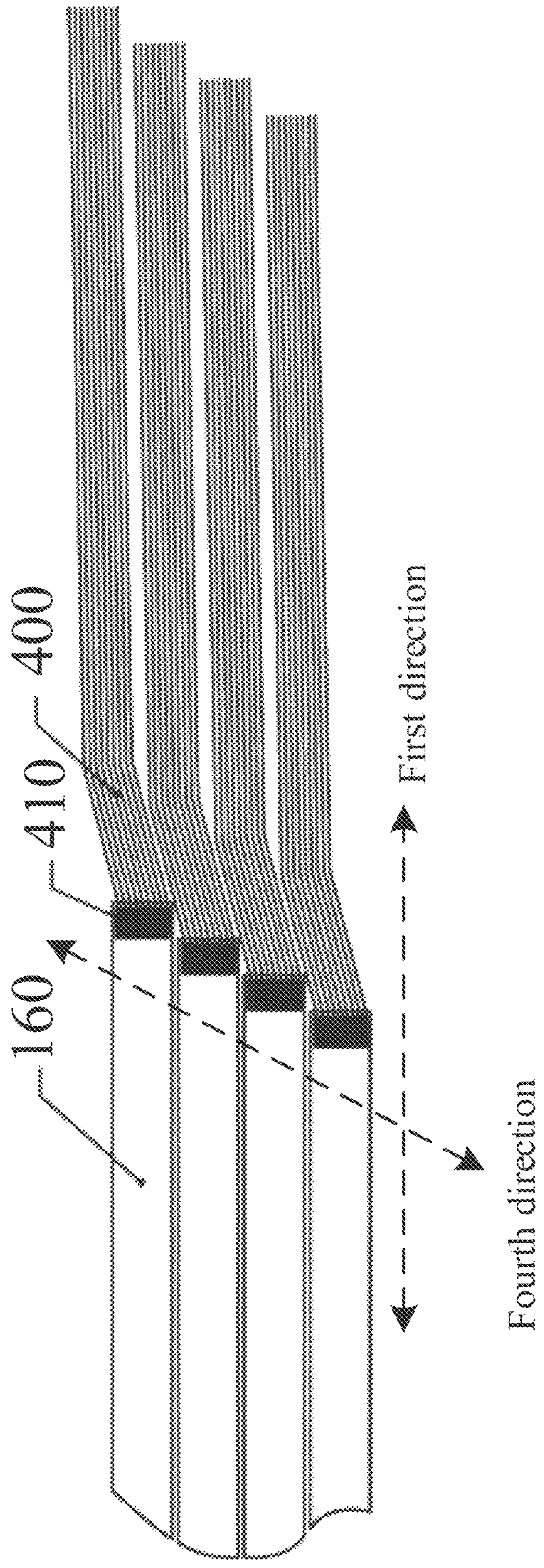
FIG. 4 is a schematic structure diagram showing that electrical connection leads and cables are soldered to form solder joints according to embodiments of the present disclosure.

In alternative embodiments as shown in FIG. 3, the support member 300 is directly connected to the transducer 100, for example, through adhesive bonding, snap-fit, or other mechanical connection means, without requiring engagement between a protrusion and a groove arranged on the first surface 303 of the support member 300 and the second surface 102 of the transducer 100 as shown in FIG. 1. In this embodiment, the transducer 100 can also be connected to the housing 200 through the support member 300.

Specifically, as shown in FIGS. 1-4, the ultrasonic probe also includes cables 400 extending through the housing 200. The electrical connection layer 120 is connected with electrical connection leads 160, and the electrical connection leads 160 are connected with the cables 400. The electrical connection leads 160 are provided in multiple, and the cables 400 are provided in multiple. The multiple electrical connection leads 160 and the multiple cables 400 are arranged at intervals along a fourth direction and are soldered in one-to-one correspondence to form solder joints 410. The fourth direction is at an angle with respect to the first direction, and the first direction is the length direction of the housing 200. In the fourth direction, two adjacent solder joints 410 are staggered. By configuring the cables 400, one end of the cables 400 is connected to the electrical connection leads 160 led out from the electrical connection layer 120, while the other end is connected to an external device. The connection between the transducer 100 and the external device through the cables 400 allows for transmitting the ultrasonic signals received by the transducer 100 to the external device. With the multiple cables 400 and the multiple electrical connection leads 160 arranged at intervals along the fourth direction, adjacent electrical connection leads 160 and cables 400 are soldered together and thus connected. Meanwhile, the staggered arrangement of adjacent solder joints 410 in the fourth direction reduces the space on the housing 200 occupied by cables 400 and the electrical connection leads 160. Additionally, the staggered arrangement of solder joints 410 reduces the spatial requirements for an internal channel within the housing 200 for the cables 400, which is beneficial for miniaturizing the ultrasonic probe.

As shown in the embodiment of FIGS. 1-4, the electrical connection leads 160 are integrated in a flexible printed circuit (FPC). One end of the FPC acts as the electrical connection layer 120 that connects the piezoelectric layer 130 to the electrical connection leads 160. Both sides of the electrical connection layer 120 that extend beyond the backing layer 110 in the axis direction of the backing layer 110 are bent downward and thus cover opposite sides of the backing layer 110, thereby saving space in the transducer 100.

It should be noted that the fourth direction is not specifically defined and can be any direction at an angle with respect to the first direction. For example, in some embodiments, the multiple cables 400 and multiple electrical connection leads 160 are arranged at intervals along the second direction. The adjacent cables 400 and electrical connection leads 160 in the first direction are soldered together, and two adjacent solder joints are staggered in the second direction.

It should be noted that there are two types of structures for the electrical connection leads 160. One type is an independent component, with two ends of the electrical connection leads 160 connected to the electrical connection layer 120 and cables 400 respectively, as described above. The other type is an integrated structure of the electrical connection leads 160 and the electrical connection layer 120, which eliminates the need for a connecting structure that connects the electrical connection leads 160 and the electrical connection layer 120.

Figure 5:
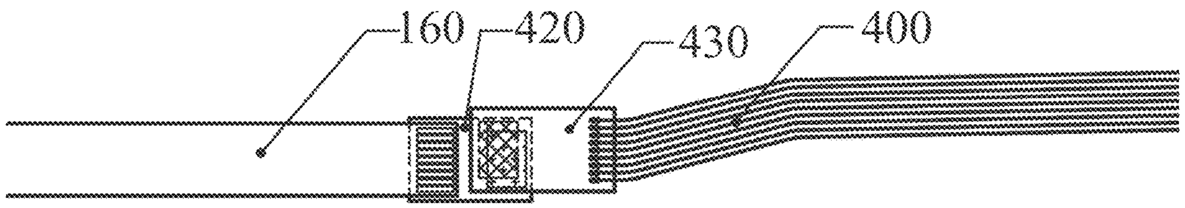
FIG. 5 is a schematic structure diagram showing that electrical connection leads and cables are connected through a connector assembly according to embodiments of the present disclosure.

In some embodiments, as shown in FIG. 5, the electrical connection leads 160 and the cables 400 are connected through a connector assembly. The connector assembly includes a male connector 420 and a female connector 430 that are engaged with each other, with one of the male connector 420 and the female connector 430 being arranged on the electrical connection leads 160, and the other arranged on the cables 400. The male connector 420 and the female connector 430 are mated to connect the electrical connection leads 160 and cables 400.

In some embodiments, as shown in FIG. 5, there are multiple electrical connection leads 160, multiple cables 400, and multiple connector assemblies. The multiple electrical connection leads 160 and multiple cables 400 are each arranged at intervals along the fourth direction, and the adjacent electrical connection lead 160 and cable 400 are connected through a single connector assembly. Two adjacent connector assemblies are staggered in the fourth direction.

Figure 6:
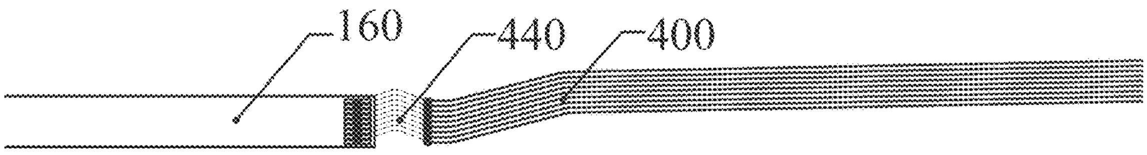
FIG. 6 is a schematic structure diagram showing that electrical connection leads and cables are connected through bonding wires according to embodiments of the present disclosure.

In some embodiments, the connector assemblies include bonding wires. As shown in FIG. 6, the electrical connection leads 160 and the cables 400 are connected by bonding wires 440.

In some embodiments, as shown in FIG. 6, there are multiple electrical connection leads 160, multiple cables 400, and multiple bonding wires 440. The multiple electrical connection leads 160 and multiple cables 400 are each arranged at intervals along the fourth direction, and the adjacent electrical connection lead 160 and cable 400 are connected through a single bonding wire. Two adjacent bonding wires are staggered in the fourth direction.

The present disclosure also provides an ultrasound diagnostic device, including an external device and the ultrasound probe as described above. The external device may be a host, which is well known to the persons skilled in the art. The cables 400 of the ultrasound probe are connected to the external device through, for example, a connector, thereby enabling information communication between the ultrasound probe and the external device.

The technical features of the above-mentioned embodiments can be combined arbitrarily. In order to keep the description concise, the present disclosure does not describe all possible combinations of technical features in the above embodiments. However, as long as there are no contradictions in the combination of these technical features, it should be considered within the scope of this specification.

The above embodiments only express several implementations of the present disclosure for which relatively specific and detailed descriptions are given. However, it should not be understood as limiting the scope of the patent application. It should be noted that those of ordinary skills in the art can make various modifications and improvements without departing from the concept of the present disclosure, which are all within the scope of protection of the present disclosure, and the protection scope of the present patent application should be determined based on the appended claims.

What is claimed is:

1. An ultrasonic probe, comprising:

a transducer, configured to transmit and receive ultrasonic signals;

a housing;

a support member, comprising one end connected to the housing and another end connected to the transducer; and a positioning arrangement, comprising a positioning groove and a positioning protrusion;

wherein the support member is arranged within a receiving cavity formed by at least one of the transducer or the housing and connected to a cavity wall of the receiving cavity, the cavity wall of the receiving cavity is provided with an adhesive sump extending along a second direction, the support member is located within the adhesive sump, the adhesive sump is configured to receive adhesive connecting the support member and the housing, the second direction is perpendicular to a first direction and the first direction is a length direction of the housing, one of the positioning groove and the positioning protrusion is provided on a sump wall of the adhesive sump and the other of the positioning groove and the positioning protrusion is provided on the support member, and the positioning protrusion engages with the positioning groove.

2. The ultrasonic probe according to claim 1, wherein the support member has a protrusion, and the transducer has a groove, the protrusion engaging with the groove.

3. The ultrasonic probe according to claim 2, wherein the support member has a first surface and the transducer has a second surface, the first surface is provided with the protrusion and the second surface is provided with the groove, and the first surface is inclined relative to a first direction to define an installation angle of the transducer, where the first direction is a length direction of the housing.

4. The ultrasonic probe according to claim 2, wherein the support member has a first surface and the transducer has a second surface, the first surface is provided with the protrusion and the second surface is provided with the groove, the first surface comprises two first surface parts, the protrusion or the groove is arranged between the two first surface parts, and an angle formed by the two first surface parts is greater than or equal to a field of view angle of the ultrasonic probe.

5. The ultrasonic probe according to claim 2, wherein the protrusion has a curved surface protruding outwardly, and the groove has a curved surface recessed inwardly.

6. The ultrasonic probe according to claim 1, wherein the support member is made of a thermally conductive material.

7. The ultrasonic probe according to claim 1, further comprising a heat dissipation device arranged inside the housing, wherein the support member is made of a thermally conductive material and connected to the heat dissipation device.

8. The ultrasonic probe according to claim 1, wherein the transducer comprises a curved backing layer connected to the support member, with an axial direction of the backing layer being perpendicular to the second direction and the first direction.

9. The ultrasonic probe according to claim 1, wherein the transducer comprises a backing layer, an electrical connection layer, a piezoelectric layer, a matching layer, and an acoustic lens layer sequentially arranged and connected, the backing layer is connected to the support member, and at least one end of the acoustic lens layer extends into and engages with the housing.

10. The ultrasonic probe according to claim 9, further comprising cables extending through the housing, wherein the electrical connection layer is connected with electrical connection leads, and the electrical connection leads are connected with the cables;

the electrical connection leads are provided in multiple, the cables are provided in multiple, the multiple electrical connection leads and the multiple cables are arranged at intervals along a fourth direction, and the multiple electrical connection leads and the multiple cables are soldered to form solder joints in one-to-one correspondence, where the fourth direction forms an angle with respect to the first direction and the first direction is a length direction of the housing; and adjacent two of the solder joints are staggered in the fourth direction.

11. The ultrasonic probe according to claim 9, further comprising cables extending through the housing, wherein the electrical connection layer is connected with electrical connection leads, and the electrical connection leads are connected with the cables through a connector.

12. An ultrasonic diagnostic device, comprising an ultrasonic probe, wherein the ultrasonic probe comprises:

a transducer, configured to transmit and receive ultrasonic signals;

a housing;

a support member, comprising one end connected to the housing and another end connected to the transducer; and a positioning arrangement, comprising a positioning groove and a positioning protrusion;

wherein the support member is arranged within a receiving cavity formed by at least one of the transducer or the housing and connected to a cavity wall of the receiving cavity, the cavity wall of the receiving cavity is provided with an adhesive sump extending along a second direction, the support member is located within the adhesive sump, the adhesive sump is configured to receive adhesive connecting the support member and the housing, the second direction is perpendicular to a first direction and the first direction is a length direction of the housing, one of the positioning groove and the positioning protrusion is provided on a sump wall of the adhesive sump and the other of the positioning groove and the positioning protrusion is provided on the support member, and the positioning protrusion engages with the positioning groove.

13. The ultrasonic diagnostic device according to claim 12, wherein the support member has a protrusion, and the transducer has a groove, the protrusion engaging with the groove.

14. The ultrasonic diagnostic device according to claim 13, wherein the support member has a first surface and the transducer has a second surface, the first surface is provided with the protrusion and the second surface is provided with the groove, and the first surface is inclined relative to a first direction to define an installation angle of the transducer, where the first direction is a length direction of the housing.

15. The ultrasonic diagnostic device according to claim 13, wherein the support member has a first surface and the transducer has a second surface, the first surface is provided with the protrusion and the second surface is provided with the groove, the first surface comprises two first surface parts, the protrusion or the groove is arranged between the two first surface parts, and an angle formed by the two first surface parts is greater than or equal to a field of view angle of the ultrasonic probe.

16. The ultrasonic diagnostic device according to claim 12, wherein the support member is arranged within a receiving cavity formed by at least one of the transducer or the housing and connected to a cavity wall of the receiving cavity.

17. An ultrasonic probe, comprising:

a transducer, configured to transmit and receive ultrasonic signals;

a housing;

a support member arranged within the housing and supporting the transducer, wherein the support member has a protrusion, and the transducer has a groove, the protrusion engaging with the groove; and a positioning arrangement, comprising a positioning groove and a positioning protrusion;

wherein the support member is arranged within a receiving cavity formed by at least one of the transducer or the housing and connected to a cavity wall of the receiving cavity, the cavity wall of the receiving cavity is provided with an adhesive sump extending along a second direction, the support member is located within the adhesive sump, the adhesive sump is configured to receive adhesive connecting the support member and the housing, the second direction is perpendicular to a first direction and the first direction is a length direction of the housing, one of the positioning groove and the positioning protrusion is provided on a sump wall of the adhesive sump and the other of the positioning groove and the positioning protrusion is provided on the support member, and the positioning protrusion engages with the positioning groove.

* * * * *